United States Patent [19]

Kodama et al.

[11] 4,239,905
[45] Dec. 16, 1980

[54] 1-β-D-ARABINOFURANOSYLCYTOSINE-5'-OLEYL PHOSPHATE AND SALTS THEREOF

[75] Inventors: Kenjiro Kodama; Manami Morozumi, both of Choshi, Japan

[73] Assignees: Yamasa Shoyu Kabushiki Kaisha, Choshi; Mineo Saneyoshi, Sapporo, both of Japan

[21] Appl. No.: 49,636

[22] Filed: Jun. 18, 1979

[30] Foreign Application Priority Data

Jun. 20, 1978 [JP] Japan ................................. 53-73699

[51] Int. Cl.$^3$ ...................... C07H 17/00; C07H 15/12
[52] U.S. Cl. ........................................ 536/29; 424/180
[58] Field of Search .................... 536/29, 23; 424/180

[56] References Cited

U.S. PATENT DOCUMENTS 3,284,440  11/1966  Patchett et al. ........................ 536/29

OTHER PUBLICATIONS

Reports on the Proceedings of the 35th Annual Meeting of the Japanese Cancer Association, p. 133, No. 476, 1976.

*Primary Examiner*—Johnnie R. Brown
*Assistant Examiner*—Blondel Hazel
*Attorney, Agent, or Firm*—Wenderoth, Lind & Ponack

[57] ABSTRACT

A new composition of matter, 1-β-D-arabinofuranosylcytosine-5'-oleyl phosphate, represented by the structural formula

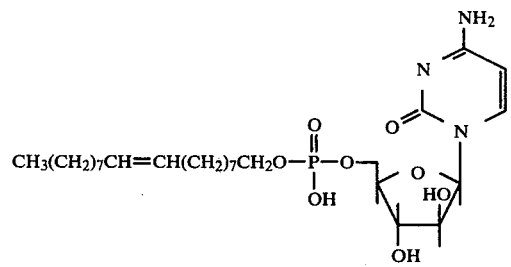

and its pharmaceutically-acceptable salts exhibit antitumor properties and are especially useful for oral administration thereof.

2 Claims, No Drawings

1-β-D-ARABINOFURANOSYLCYTOSINE-5'-OLEYL PHOSPHATE AND SALTS THEREOF

BACKGROUND OF THE INVENTION

1. Field of the Invention

This invention relates to a novel substance, 1-β-D-arabinofuranosylcytosine-5'-oleyl phosphate (hereinafter referred to as ara-CMP oleyl ester) and its pharmaceutically-acceptable salts, these substances having excellent antitumor properties.

2. Prior Art

It has been known that 1-β-D-arabinofuranosylcytosine (hereinafter referred to as ara-C) is an agent which is indispensable for chemotherapy of cancers, especially leukemias such as acute lymphatic leukemia (ALL), acute myelogenous leukemia (AML) and meningoleukemia. Recently, ara-C has been often employed in combination with other agents, for example, in DCMP (daunomycin-ara-C-mitomycin-predonisolone) therapy and MFC (mitomycin-5-fluorouracil-ara-C) therapy. Thus, ara-C has been often used as an essential agent of combined therapeutics in the chemotherapy of leukemias as well as solid cancers such as lymphoma, gastric and intestinal cancers and adenocarcinoma (e.g., reference is made to "Chemotherapeutics of Cancers", Yakuzai Koza Vol. 1, p.p. 75-80, compiled by H. Niitani and H. Kanagami, published by Clinic Magazine Company, Japan, July 1, 1977). At the moment, however, ara-C can only be used for intravenous or intramuscular injection from a viewpoint of pharmacodynamics and actually cannot be used for oral administration. This fact has been an obstacle to further extensive applications of ara-C. Especially, its continuous administration by intravenous injection causes physical and mental pain to a considerable extent in patients. Thus, the development of forms of ara-C which can be administered orally has been urgently needed in the clinical field.

Hitherto, the syntheses of ara-C derivatives which can be administered orally have been tried (cf J. Med. Chem. Vol. 19, No. 8, p.p.1013–1016, 1976). It has also been reported that the oral administration of ara-C is effective in combination with a cytidinedeaminase inhibitor such as tetrahydrouridine (cf. Cancer Research, Vol. 30, p.p 2166–2172, 1970). However, the effects are not remarkable and there has been no prospect of practical use of this administration.

On the one hand, the present inventor has synthesized alkyl or aryl esters of arabinofuranosylcytosine-5'-phosphate (hereinafter referred to as ara-CMP) in order to study improvement in so-called bio-availability of the ara-C derivatives such as their resistivity to cytidinedeaminase, their effects on ara-C-resistant strains, and their antitumor properties based on selective affinity for organs. These esters were tested with respect to their antitumor properties (cf. Reports on the proceedings of the 35th annual meeting of the Japanese Cancer Association, p.133, No.476, issued by Nippon Gan Gakkai, Sept. 1, 1976). The esters of ara-CMP, however, only showed a weaker activity than ara-C and ara-CMP in cell proliferation-inhibition effects in vitro using L5178Y cells. Also, in the antitumor tests in vivo using mouse-leukemia cell L1210, the esters tested only showed an increase in life span similar to or lower than that or ara-CMP when they were administered intraperitoneally. The alkyl esters having 11 or more carbon atoms in the alkyl moiety showed some effectiveness in that the effective doses were decreased but were accompanied by an increase in toxicity. On the whole, in both in vitro experiment and intraperitoneal administration, pharmacologically useful improvements in ara-C or ara-CMP were not observed over the ara-CMP esters.

SUMMARY OF THE INVENTION

The present inventors have carried out extensive research on a novel medicine and dosage form, derived from ara-C, which exhibit marked antitumor properties in non-injection administration such as oral administration and have low toxicity. The present invention is based on the finding that the novel compound ara-CMP oleyl ester has excellent antitumor and pharmacological properties. Thus, the present invention relates to the ara-CMP oleyl ester represented by the following structural formula and its pharmaceutically-acceptable salts, which are useful as excellent antitumor agents.

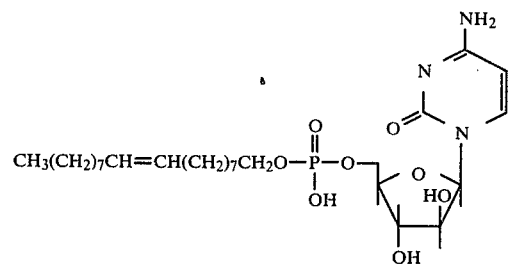

DETAILED DESCRIPTION OF THE INVENTION

The pharmaceutically-acceptable salts of ara-CMP oleyl ester are exemplified by their alkali metal (e.g., sodium, potassium) salts, alkaline earth metal (e.g., calcium, magnesium) salts, and ammonium salt.

The process for preparing the ara-CMP oleyl ester is not especially restricted in this invention. One of the representative processes for the preparation is, for example, to mix (A) the ara-CMP salt which has been protected at its $N^4$-, $O^{2'}$- and/or $O^{3'}$-positions with an acyl group (e.g., acetyl, butyryl, benzoyl groups) and (B) oleyl alcohol to condense. The condensation reaction is accelerated by an arylsulfonyl chloride in an organic solvent or mixed organic solvents (as disclosed in the specification of Japanese Laid-Open Pat. No. 899681/1977).

Examples of the ara-CMP salts in the above mentioned process are tertiary alkylammonium salts such as triethylammonium salt, tri-n-butylammonium salt, tri-n-octylammonium salt, quaternary alkylammonium hydroxide salts such as methyl-tri-n-butylammonium hydroxide salt, methyl-tri-n-octylammonium hydroxide salt, and amidine salts such as 4-morpholino-N,N'-dicyclohexylcarboxamidine salt. Examples of the organic solvents are N,N-dimethylformamide, N,N-dimethylacetamide, chloroform, pyridine, dioxane, tertahydrofuran, ethyl acetate, tri-n-butylamine, and mixtures thereof. Examples of the arylsulfonyl chlorides are triisopropyl-benzenesulfonyl chloride, o-tosyl chloride, p-tosyl chloride, benzenesulfonyl chloride, 2-mesitylenesulfonyl chloride.

The reaction conditions are, for example, in pyridine, 1 to 2 hours at room temperature when p-tosyl chloride is used as the condensation agent, and 1 to 20 hours at room temperature when tri-isopropyl-benzenesulfonyl chloride is used.

The resulting ara-CMP oleyl ester can be isolated from the reaction mixture and purified according to conventional methods, for example, by suitably selecting and combining purification procedures such as liquid-liquid extraction, ion-exchange chromatography, adsorption chromatography and recrystallization. The salts of ara-CMP oleyl ester can also be prepared in accordance with conventional processes. The pharmacological activity tests of ara-CMP oleyl ester will now be described.

EXAMPLE OF ACTIVITY TEST (Therapeutic test on L1210 leukemia)

The L1210 leukemic cell suspension ($1 \times 10^5$ cells/0.2 ml) was implanted intraperitoneally in $BDF_1$ mice (males, 18 to 22 g, females, 16 to 20 g) (7 mice per group). From 24 hours after the implantation to the 5th day thereafter, the predetermined doses of the compounds to be tested were orally administered to the mice successively once a day. The compounds to be tested were dissolved or suspended in a phosphate buffered salt solution (PBS) containing 0.5% carboxymethylcellulose, and given at a dose rate of 0.1 ml per 10 g of the mouse's body weight. To a control group, only the same solvent as used for the dissolution of the compounds to be tested was administered in the same way. The mean survival times (MST) for each group were calculated, and the corresponding increase in life span (%ILS) was obtained in accordance with the following formula, the results of which are shown in Table 1.

TABLE 1

$$\% \text{ ILS} = \left( \frac{\text{MST of the treated group}}{\text{MST of the control group}} - 1 \right) \times 100$$

| Compound to be tested | % ILS at dose (mg/kg/day) of | | | | | | |
|---|---|---|---|---|---|---|---|
| | 6.25 | 12.5 | 25 | 50 | 100 | 200 | 400 |
| ara-C (hydrochloride) | | | | | 22 | 34 | 67 |
| ara-CMP | | | | 8 | 21 | 57 | 73 |
| ara-CMP oleyl ester | 20 | 39 | 54 | 96 | 109 | 120 | >159* |

*The symbol (>) means that some mice survived the test period (30 days).

As is clear from the results shown in Table 1, ara-CMP oleyl ester has excellent pharmacological properties by oral administration in that, in comparison with ara-C and ara-CMP, the oleyl ester exhibits a far greater maximum increase in life span (ILS max), a higher therapeutic index [maximum increase in life span (ILS max)/30% increase in life span (ILS30)], and a satisfactory antitumor effect in a broad range of doses. It has also been confirmed that the ara-CMP oleyl ester exhibits a lower toxicity (e.g., hemolysis, etc.) than conventional ara-CMP esters such as ara-CMP stearyl ester, not only by oral administration but also by injection. Thus, ara-CMP oleyl ester can be utilized alone as an excellent antitumor agent, and is also expected to be a suitable agent in combination with other antitumor agents.

A typical example of preparation of ara-CMP oleyl ester is illustrated below.

EXAMPLE OF PREPARATION 10 ml of pyridine were added to 10 m mol of $N^4$, $O^{2'}$, $O^{3'}$-triacetyl ara-CMP (tributylammonium) salt and 5.4 g (20 m mol) of oleyl alcohol to dissolve them, and then 3.8 g (20 m mol) of p-tosyl chloride was further added thereto. The mixture was caused to react. After 2 hours, 100 ml of water and 50 ml of chloroform were added to the reaction mixture, which was then shaken. The resulting chloroform layer was taken out, and 20 ml of ammonia water and 50 ml of ethanol were added thereto to prepare a homogeneous solution. The resulting solution was allowed to stand overnight, and then water was added thereto with stirring, the reaction product thereby being extracted into the water layer. The resulting aqeuous solution was adjusted to a pH of 2.0 to 2.5 with concentrated hydrochloric acid to separate out the product (free acid).

The separated product was collected by filtration, and water was added thereto. The mixture thus obtained was adjusted with sodium hydroxide to a pH of 7 to 8. The resulting solution was again adjusted to a pH of 2.0 to 2.5 with hydrochloric acid to separate out the objective free acid. The separated free acid was collected by filtration, suspended in ethanol and stirred, filtered, and dried to obtain 4.5 g (yield 78.4%) of ara-CMP oleyl ester.

| Elementary analysis: | as $C_{27}H_{48}N_3O_8P$ |
|---|---|
| Calculated | P(%) = 5.40 |
| Found | P(%) = 5.19 |
| Melting Point: | 218–220° C. (decomposed) (free acid) |
| | 203–205° C. (decomposed) (sodium salt) |
| Thin-layer chromatography: | |
| (developing solvent:ethanol:n-butanol: 1M ammonium acetate (pH 7.5) = 2:5:3) | |
| Rf = 0.80 | |

What we claim is:

1. 1-β-D-Arabinofuranosylcytosine-5'-oleyl phosphate or a pharmaceutically-acceptable salt thereof, said phosphate being represented by the structural formula.

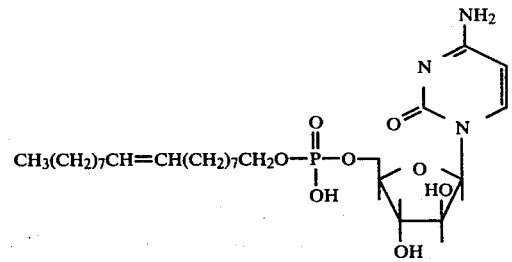

2. A salt of 1-β-D-arabinofuranosylcytosine-5'-oleyl phosphate as claimed in claim 1, which is selected from the group consisting of alkali metal salts, alkaline earth metal salts and ammonium salt.

* * * * *